United States Patent [19]

Gonzalez

[11] Patent Number: 4,599,313

[45] Date of Patent: Jul. 8, 1986

[54] **PRESERVATION OF FOODS WITH NON-LACTOSE FERMENTING *STREPTOCOCCUS LACTIS* SUBSPECIES *DIACETILACTIS***

[75] Inventor: Carlos F. Gonzalez, Sarasota, Fla.

[73] Assignee: Microlife Technics, Inc., Sarasota, Fla.

[21] Appl. No.: 593,669

[22] Filed: Mar. 26, 1984

Related U.S. Application Data

[62] Division of Ser. No. 368,724, Apr. 15, 1982, Pat. No. 4,477,471.

[51] Int. Cl.[4] ............... C12N 1/20; C12N 15/00; C12N 1/00; C12R 1/46; A23B 4/12; A23C 9/12; A23C 17/00

[52] U.S. Cl. .................. 435/253; 435/172.1; 435/172.3; 435/317; 435/885; 426/7; 426/34; 426/36; 426/38; 426/40; 426/42; 426/43; 426/61; 935/22; 935/29; 935/38

[58] Field of Search ............... 435/172.3, 253, 317, 435/885, 172.1; 426/7, 34, 36, 38, 40, 42, 43, 61; 935/22, 29, 38

[56] References Cited

U.S. PATENT DOCUMENTS

| | | | |
|---|---|---|---|
| 3,968,256 | 7/1976 | Sing | 426/38 |
| 4,172,899 | 10/1979 | Vedamuthu | 426/38 |
| 4,191,782 | 3/1980 | Vedamuthu | 426/38 |

OTHER PUBLICATIONS

Kempler et al, "Characterization of plasmid deoxyribonucleic acid in *Streptococcus lactis* subsp. *diacetylactis:* Evidence for plasmid-linked citrate utilization", Appl. Environ. Microbiol. 37: 316 (1979).

*Manual of Methods for General Bacteriology*, Gerhardt et al. (ed.), American Society for Microbiology, Washington, D.C., 1981, pp. 228, 229, and 242; 210-217.

LeBlanc et al, J. of Bacteriology, vol. 140, No. 3, pp. 1112-1115, (1979).

Kempler & McKay, Appl. Microbiol. 39, pp. 926-927, (1980).

*Primary Examiner*—Thomas G. Wiseman
*Assistant Examiner*—James Martinell
*Attorney, Agent, or Firm*—Ian C. McLeod

[57] ABSTRACT

A method for using selected strains of *Streptococcus lactis* subspecies *diacetilactis*, which have been modified to be non-lactose fermenting, for the preservation of foods containing lactose is described. The subspecies is more generally known as *Streptococcus diacetilactis*. The selected *Streptococcus diacetilactis* strains have been modified by curing to remove at least one natural plasmid which controls the fermentation of lactose to lactic acid while retaining the ability of this subspecies to inhibit bacterial spoilage in foods. The plasmid removed by curing is about 41 megadaltons (Mdal) in mass. The method using the modified strains of *Streptococcus diacetilactis* is particularly adapted for the preservation of milk products.

4 Claims, No Drawings

PRESERVATION OF FOODS WITH NON-LACTOSE FERMENTING STREPTOCOCCUS LACTIS SUBSPECIES DIACETILACTIS

This application is a division of application Ser. No. 368,724 filed Apr. 15, 1982, now U.S. Pat. No. 4,477,471.

BACKGROUND OF THE INVENTION

The present invention relates to a new method for preserving lactose containing foods with plasmid modified strains of Streptococcus lactis subspecies diacetilactis also generally known as Streptococcus diacetilactis. The useful modified Streptococcus diacetilactis strains have been cured to remove a 41 Mdal plasmid such that they are no longer able to ferment lactose to produce lactic acid which imparts an undesirable flavor and curdling with certain milk products.

PRIOR ART

The present invention particularly relates to an improvement on the inventions described in U.S. Pat. Nos. 4,172,899 and 4,191,782 to Vedamuthu wherein Streptococcus diacetilactis is described for use in Cottage cheese dressings to impart a diacetyl flavor and to inhibit spoilage. U.S. Pat. No. 3,968,256 to Sing describes a related method.

It is known that the natural or wild type (WT) Streptococcus diacetilactis, such as a strain known as 18-16, generate an inhibitory substance which reduces bacterial spoilage in dairy products, particularly fluid milk containing products, which are prone to psychrotrophic bacterial contamination and spoilage. The natural Streptococcus diacetilactis also ferment milk lactose to produce a certain amount of lactic acid and produce lactic acid in other lactose containing foods which is a disadvantage. The Streptococcus diacetilactis also ferments citrate naturally present in the milk to produce the characteristic diacetyl or butter flavor such as is present in the cream dressing on Cottage cheese. The problem is that in many of the fermented milk products the lactic acid tends to curdle the milk and impart a sour flavor. Also, there are foods where more citrate flavor is wanted without the risk of increased lactose fermentation.

Kempper and McKay have described modified strains of Streptococcus diacetilactis which are unable to ferment lactose (lac$^-$) in Applied and Experimental Microbiology Vol 37, No. 2 pages 316–323 (1979). Strains of lac$^-$ noncitrate (cit$^-$) fermenting Streptococcus diacetilactis are also described. No utility was discussed for the modified lac$^-$cit$^+$ or lac$^-$cit$^-$ Streptococcus diacetilactis strains and the primary concern was to eliminate such strains from commercial cultures.

Objects

It is therefore an object of the present invention to provide a method for the preservation of foods containing lactose from bacterial spoilage using modified strains of Streptococcus diacetilactis WT which are lac$^-$. Further it is an object of the present invention to provide a curing method whereby preferred modified lac$^-$ Streptococcus diacetilactis strains are produced by the removal of certain plasmids. Finally it is an object of the present invention to provide preferred compositions of modified lac$^-$cit$^+$ Streptococcus diacetilactis strains in admixture with a leuconostoc which ferments citrate to produce the diacetyl flavor so as to provide improved flavor development in lactose and citrate containing foods. These and other objects will become increasingly apparent from the following description.

General Description

The present invention relates to the method for the preservation of a food containing lactose by providing a culture in the food which generates a bacterial spoilage inhibitory substance the improvement which comprises: providing in the food a modified strain of Streptococcus diacetilactis which is unable to ferment lactose to lactic acid as a result of the removal of a naturally occurring 41 Mdal plasmid from a strain of Streptococcus diacetilactis containing the plasmid, wherein the modified strain produces the inhibitory substance.

The present invention also relates to the method of removing a natural about 41 megadalton plasmid and then a natural about 5.5 megadalton plasmid from a strain of Streptococcus diacetilactis containing the plasmids and having the ability to ferment lactose to lactic acid with the 41 Mdal plasmid and having the ability to ferment citrate to diacetyl with the 5.5 Mdal plasmid which comprises: exposing the cells to elevated temperatures, preferably about 40° C. and between about 32° and 60° C., to remove the 41 Mdal plasmid from the cells; contacting the resulting cells of Streptococcus diacetilactis with a sub-lethal, curative level of a plasmid curing agent to remove the 5.5 Mdal plasmid, wherein the Streptococcus diacetilactis without the 41 and 5.5 Mdal plasmids produces a substance which inhibits bacterial spoilage in foods.

Finally the present invention relates to a bacterial composition which comprises in admixture: (a) cells of a Streptococcus diacetilactis which is unable to ferment lactose to lactic acid as a result of the removal of a plasmid measuring about 41 Mdal from a strain of Streptococcus diacetilactis containing the plasmid and which produces diacetyl flavor from citrate and which inhibits bacterial spoilage in foods; and (b) a culture of a leuconostoc, such as Leuconostoc cremoris, which generates a diacetyl flavor from citrate in milk, wherein the ratio of (a) to (b) is between about 0.1 to 9.9 and 9.9 to 0.1.

The present invention also relates to removal of naturally occurring plasmids from a strain of Streptococcus diacetilactis the strains ability to ferment lactose to form lactic acid has been linked to the presence of a 41 Mdal plasmid. Additionally, the strains ability to utilize the citrate to produce diacetyl has been linked to a 5.5 Mdal plasmid. Exposure of the WT strain to elevated temperatures, preferably 40° C. and between about 32° C. and 60° C., can be used to remove the 41 Mdal plasmid. Growth of the resulting cells of the lac$^-$ Streptococcus diacetilactis in the presence of sub-lethal curative level of a plasmid curing agent did remove the 5.5 Mdal plasmid. The resulting strains (lac$^-$, cit$^-$) not containing the 41 and 5.5 plasmids produce the inhibitory substance, at the same level as the parent WT strain.

The modified Streptococcus diacetilactis strains are characterized as lactose negative (lac$^-$) and citrate positive or negative (cit$^+$ or cit$^-$). The preferred curing method removes both 41 Mdal and a 5.5 Mdal plasmids. Streptococcus diacetilactis WT has six (6) natural plasmids which are about 41, 28, 6.4, 5.5, 3.4 and 3.0 Mdal in molecular weight. The usual Streptococcus diacetilactis WT strain is referred to as 18-16, ATCC 15,346 (American Type Culture Collection). Other useful strains are Streptococcus diacetilactis 26-2, Streptococcus diacetilactis DRC-1, *Streptococcus diacetilactis* DRC-2 and *Streptococcus diacetilactis* DRC-3. These strains produce a bacterial inhibitory substance (INS+).

To prepare the modified strains, a 6-pla+, lac+, cit+, INS+ *Streptococcus diacetilactis* WT was used. This strain is particularly useful at low temperatures in developing flavor in Cottage cheese cream dressing. The 6-pla+, lac+, cit+ INS+ *Streptococcus diacetilactis* WT was cured at elevated temperatures in a liquid growth medium and a 5-pla+, lac−, cit+, INS+ *Streptococcus diacetilactis* was produced. The elevated temperature was about 40° C., preferably between 32° C. and 60° C. The 41 Mdal plasmid was removed. Optionally a curing agent was used to remove the 5.5 Mdal plasmid from the 5-pla+, lac−, cit+, INS+ strain at a sub-lethal concentration level so that it was not killed. Suitable curing agents for the 5-pla+, lac−, cit+, INS+ *Streptococcus diacetilactis* were for instance ethidium bromide, acriflavin and acridine orange. The product was a 4-pla+, lac−, cit−, INS+ *Streptococcus diacetilactis*.

Additionally, the 4-pla+, lac−, cit−, INS+ *Streptococcus diacetilactis* was cured by growth at elevated temperatures in liquid medium and a 3-pla+, lac−, cit−, INS+ *Streptococcus diacetilactis* was obtained. The elevated temperature was about 40° C., preferably between 32° C. and 60° C. The 28 Mdal plasmid was removed and no change in phenotypic characteristic has been observed as a result of removal of this 28 Mdal plasmid.

Plasmid profiles were determined by lysis and agarose gel electrophoresis on the parent WT strain and the modified strains as described in LeBlanc et al., *J. of Bacteriology* Vol. 140, No. 3, pages 1112 to 1115 (1979). It was found that the 41 Mdal plasmid was removed in the first curing step, then the 5.5 Mdal plasmid was removed in the second curing step and then the 28 Mdal plasmid was removed in the third curing step. The size of the removed plasmids was determined based upon comparisons with known size standards in parallel electrophoresis patterns.

The resulting modified *Streptococcus diacetilactis* strains were concentrated to at least about $1 \times 10^8$ cells per ml and then used to preserve refrigerated foods which contain lactose. The cultures were tested to be certain that they were INS+. The modified *Streptococcus diacetilactis* were used in substantially pure form. The lac−, cit+, INS+ strain was mixed with other diacetyl flavor producing bacteria, particularly the leuconostocs, for enhanced flavor production.

Various culture preservation agents can be used as is known in the prior art. Glycerol is preferred for frozen concentrates as a freezing stabilizing agent to maintain the viability of the cells on freezing and during storage. Lyophilized bacterial concentrates can also be used.

Specific Description

The following example shows the steps in the isolation, concentration and use of the modified *Streptococcus diacetilactis*.

EXAMPLE 1

(1) Sugar Utilization. The following plating medium was used to detect the sugar fermentation characteristics of an isolated strain:

(a) Basal Sugar Medium (BSM) was used for plating of *Streptococcus diacetilactis* to show sugar fermentation. Fermentation of sugars added to the medium is shown by color change of a purple color to yellow as a result of the lowered pH due to acid production from the sugars. The pH change occurs at pH 5.2.

| | |
|---|---|
| Tryptone | 20 grams |
| Yeast extract | 5 grams |
| Gel | 2.5 grams |
| Sodium acetate | 1.5 grams |
| Sodium chloride | 4.0 grams |
| Agar | 15 grams |
| 10 ml of 0.4% Bromocresol Purple (BCP) | |
| Water | 1000 ml |

After heat treatment of 15 minutes at 121° C., a filter-sterilized (0.2 μfilter) solution of concentrated carbohydrate (20% w/v) was aseptically added to give a final concentration of 0.5% (w/v) carbohydrate in the BSM medium.

The medium was aseptically poured into petri dishes and allowed to solidify at room temperature.

(b) Supplemental Sugars added to Medium (BSM) for determining sugar fermentation characteristics were:

BSM+glucose=BG

BSM+lactose=BL (c) The starting *Streptococcus diacetilactis* WT strains were tested against these sugars to insure that they were active in generating acid with glucose and other sugars including lactose. The modified strains were also tested for loss of a sugar fermentation characteristic.

(d) Aerobic incubation was determined to be satisfactory to show lactic acid produced. Anaerobic conditions can be used.

(2) Citrate Utilization. Citrate utilization was determined by plating on a medium and using a procedure as described in Kempler and McKay *Appl. Microbiol.* 39 pages 926 and 927 (1980) and referred to as CM. The medium was as follows:

Solution A 10 gram nonfat dry milk
2.5 gram yeast extract
5 gram dextrose
15 gram agar
980 ml of water.

The pH was adjusted to pH 6.6. The mixture was autoclaved for 12 minutes at 10 pounds of steam pressure.

Solution B

Solution B contained 10% potassium ferrocyanide.

Solution C

Solution C contains 1 gram ferric citrate and 1 gram of sodium citrate in 40 ml of water. The solutions were steamed at 100° C. for 30 minutes. Solution A was tempered at 50° C. and 10 ml of each of B and C was added and then poured onto sterile Petri dishes.

The citrate ion inhibits the reaction between ferric ion and potassium ferrocyanide. When a bacterial colony uses citrate, the ferric ion is freed to react and forms Prussian blue with the potassium ferrocyanide. Citrate utilizing colonies are blue. Non-citrate utilizing colonies are white.

(3) Curing

The steps in the isolation of modified *Streptococcus diacetilactis* strains were:

(a) Grow the *Streptococcus diacetilactis* WT overnight in sterile Elliker broth (Difco).

(b) Inoculate *Streptococcus diacetilactis* WT overnight broth culture into tubes of sterile Elliker broth.

(c) Incubate at 40° C. as a first curing step (preferably between about 32° C. and 60° C. in a water bath and in the dark for between about 18 and 24 hours to remove the 41 Mdal plasmid (which renders the strain lac−). (An alternate method is to use curing agents such as acriflavin or ethidium bromide at increasing concentrations at 32° C. in order to obtain lac− strains.)

Optionally a second curing step was performed to remove the 5.5 Mdal plasmid which renders the strain cit− with acridine orange (AO) in a growth medium in increasing concentrations at 32° C. The concentrations are preferably between about 5 and 50 micrograms per milliliter. A third curing step was performed to remove the 28 Mdal plasmid, which, at the present time, has no assigned function, by incubation at 40° C. in a water bath and in the dark for about 18 to 24 hours.

(d) Read the tubes for growth in the presence of AO; and (e) Plate the resulting strains which grow on BL as described in paragraph 1 to detect lac−strains.

(f) Determine whether the cells are cit+ or cit− in CM.

(g) Determine whether the strains continue to be INS+. Using this method and testing in BL and CM, several lac−, cit+ strains and then lac−, cit− strains were isolated. The absence of the 41 and 28 Mdal plasmids as a result of elevated temperature curing and a 5.5 Mdal plasmid as a result of the use of the curing agent was subsequently confirmed by agarose gel electrophoresis patterns using the LeBlanc et al procedure.

Table I shows the plasmid composition of the modified strains compared to 18-16 WT (ATCC 15,346).

TABLE I

|  | Plasmids (Mdal) | | | | | |
|---|---|---|---|---|---|---|
|  | 41 | 28 | 6.4 | 5.5 | 3.4 | 3.0 |
| 18-16WT | X* | X | X | X | X | X |
| NRRL-B-15005*** | —** | X | X | X | X | X |
| NRRL-B-15006**** | — | X | X | — | X | X |
| NRRL-B-15018 | — | — | X | — | X | X |
| GK-5 | — | X | X | — | X | — |

\* = plasmid present
\*\* = plasmid absent
\*\*\* = common properties with GK 1, 2 and 4 of Kempler and McKay which is lac−, cit+.
\*\*\*\* = similar to GK-5 of Kempler and McKay also which is a lac−, cit− strain but containing a 3.0 Mdal plasmid not present in the Kempler and McKay strains.

The cultures were also tested for the production of INS+. This was accomplished by duplicate inoculation of the strains to be tested onto a plate of BG agar.

The plates were incubated at 25° C. and 32° C. for 18 hr. An overlay of BHI(Difco) agar (0.7%) containing *Pseudomonas fluorescens* or *Alcaligenes metalcaligenes* was made over the incubated plates. A zone of inhibition developed around the points where strains of *Streptococcus diacetilactis* were inoculated on the dishes. It was found that strains NRRL-B-15005, NRRL-B-15006 and NRRL-B-15018 were as inhibitory as *Streptococcus diacetilactis* 18-16. Lac−, cit+ NRRL-B-15005, lac−, cit− NRRL-B-15006 and lac−, cit− NRRL-B-15018 were deposited with the NRRL in Peoria, Ill. (4) Bacterial Concentrates. Bacterial concentrates of NRRL-B15005 and NRRL-B-15006 were prepared as described in U.S. Pat. Nos. 4,172,899 and 4,191,782 to Vedamuthu. The cells were grown in the following medium:

| Yeast extract | 1.6% (w/w) |
| Dextrose | 2.5% (w/w) |
| Casein digest (HYCASE ®) | 0.72% (w/w) |

-continued

| Monopotassium phosphate | 0.54% (w/w) |
| Disodium phosphate | 0.35% (w/w) |
| Magnesium sulfate | 50 g per 1135.5 liters |
| Manganese sulfate | 25 g per 1135.5 liters |
| Ferric sulfate | 25 g per 1135.5 liters |
| Water | 1135.5 liters |

The cells were grown to about $8.95 \times 10^9$ cells per ml. The cells were preferably concentrated by centrifugation and glycerine (10% by weight) was added. The concentrates were frozen for storage prior to use and were found to be storage stable. The concentrates contained about $2 \times 10^{11}$ cells per ml.

(5) Cottage Cheese Creaming with NRRL-B-15005

Uncentrifuged freshly grown cells of 18-16 WT and NRRL-B-15005 were used in a Cottage cheese cream dressing in the manner described in the Vedamuthu patents. The mixtures were 3788 grams of dry Cottage cheese and 2522 grams of cream mixed with 56.86 grams sodium chloride. 18-16 WT concentrates contained $6.5 \times 10^9$ cells per ml. The NRRL-B-15005 concentrate contained $4.7 \times 10^9$ cells per ml. The mixture was placed in 15 oz. cups each of which held 300 grams. The initial pH of the Cottage cheese mixture was 5.25 and the NRRL-B-15005 cell count was about $9 \times 10^5$ cells per gram of Cottage cheese after addition of the cells. The stability of the creamed Cottage cheese held at 10° C. was observed over time with and without added *Pseudomonas fragii* as a spoilage bacterium at about $10^3$ cells per gram of Cottage cheese. It was found that NRRL-B-15005 culture was equivalent in inhibiton of spoilage to 18-16 WT and inhibited the *Pseudomonas fragii* for an equivalent period of time.

(6) Cottage Cheese Creaming with NRRL-B-15006

Concentrates of NRRL-B-15006 and 18-16 WT were used in Cottage cheese cream dressing in a manner similar to 5 above. The mixtures were 300 grams of dry Cottage cheese curd and 180 grams of cream (Half and Half). The concentrate of NRRL-B-15006 contained $2 \times 10^{11}$ cells per ml. Sufficient concentrate of NRRL-B-15006 was added to final concentration of about $1.32 \times 10^6$ cells per gram of creamed curd. Sufficient concentrate of 18-16 WT was added to final concentration of about $1.3 \times 10^6$ cells per gram of creamed curd. The inoculated creamed Cottage cheese was placed in plastic containers and *Pseudomonas fluorescens* was added as a spoilage bacterium at about $10^3$ cells per gram of creamed Cottage cheese.

Controls contained no added *Pseudomonas fluorescens*. The containers of creamed Cottage cheese were held at 10° C. and examined organoleptically overtime for spoilage. It was found that NRRL-B-15006 was equivalent to 18-16WT in inhibition of spoilage of cheese containing added *Pseudomonas fluorescens* and inhibited the *Pseudomonas fluorescens* for an equivalent period of time. The lac−, cit− NRRL-B-15006 developed no diacetyl flavor during time period that Cottage cheese was held at 10° C.

(7) Refrigerated Milk

Concentrates of NRRL-B-15006 lac− and cit− and 18-16 WT were added to freshly bottled skim milk obtained from local dairy. Sufficient concentrate of NRRL-B-15006 was added to final concentration of about $1 \times 10^6$ cells per ml of skim milk. Sufficient concentrate of 18-16 WT was added to final concentration of about $1 \times 10^6$ cells per ml of skim milk. The inoculated skim milk along with inoculated control was placed in sterile flasks and were held at 10° C.

Titratable acidity was determined for the skim milk along with organoleptic evaluation for spoilage at various time intervals. The results were as follows:

| Days Held At 10° C. | UNINOCULATED CONTROL SKIM MILK | | | SKIM MILK INOCULATED WITH NRRL-B-15006 | | | SKIM MILK INOCULATED WITH 18-16 WT | | |
|---|---|---|---|---|---|---|---|---|---|
| | TA | Developed Acidity | Organoleptic Evaluation For Spoilage | TA | Developed Acidity | Organoleptic Evaluation For Spoilage | TA | Developed Acidity | Organoleptic Evaluation For Spoilage |
| 0 | 0.15 | — | Fresh | 0.15 | — | Fresh | 0.15 | — | Fresh |
| 5 | 0.17 | 0.02% | Fresh | 0.15 | — | Fresh | 0.15 | — | Fresh |
| 8 | 0.19 | 0.04% | Fresh | 0.15 | — | Fresh | 0.19 | 0.04% | Fresh |
| 9 | 0.20 | 0.05% | Fresh | 0.15 | — | Fresh | 0.29 | 0.14% | Fresh |
| 10 | 0.21 | 0.06% | Some off Odor | 0.15 | — | Fresh | 0.35 | 0.20% | Fresh |
| 12 | 0.24 | 0.09% | Spoiled | 0.17 | 0.02% | Fresh | 0.43 | 0.28% | Fresh |

Culture NRRL-B-15006 did not produce acid in skim milk stored 12 days at 10° C. during which time 18-16 WT produced an appreciable amount of acid. It was found that NRRL-B-15006 was equivalent to 18-16 WT in extending shelflife of skim milk held at 10° C.

I claim:

1. A bacterial composition which comprises in admixture:
   (a) cells of a *Streptococcus diacetilactis* which is unable to ferment lactose to lactic acid as a result of the removal of a plasmid measuring about 41 Mdal from a strain of *Streptococcus diacetilactis* containing the plasmid and which produces diacetyl flavor from citrate and which inhibits bacterial spoilage in foods wherein the *Streptococcus diacetilactis* produces an inhibitory substance for *Pseudomonas fluorescens;* and
   (b) cells of a leuconostoc bacterium which generates a diacetyl flavor from citrate in milk, wherein the ratio of (a) to (b) is between about 9.9 to 0.1 and 0.1 to 9.9.

2. The composition of claim 1 wherein the composition contains a freezing stabilizing agent which maintains cell viability and wherein the composition is frozen or the composition is lyophilized.

3. The composition of claim 1 containing above $10^8$ cells per ml.

4. The composition of claim 1 wherein the *Streptococcus diacetilactis* without the 41 Mdal plasmid is selected from the group consisting of *Streptococcus diacetilactis* NRRL-B-15005, NRRL-B-15006 and NRRL-B-15018.

* * * * *